(12) United States Patent
Herod

(10) Patent No.: US 6,705,153 B2
(45) Date of Patent: Mar. 16, 2004

(54) MONITORING LIQUID CHARACTERISTICS INCLUDING QUALITY CONTROL

(75) Inventor: Erman E. Herod, Clyde, TX (US)

(73) Assignee: Dynamic Solutions, Inc., Alice, TX (US)

( * ) Notice: Subject to any disclaimer, the term of this patent is extended or adjusted under 35 U.S.C. 154(b) by 0 days.

(21) Appl. No.: 10/281,016

(22) Filed: Oct. 24, 2002

(65) Prior Publication Data

US 2003/0046986 A1 Mar. 13, 2003

Related U.S. Application Data

(62) Division of application No. 09/655,048, filed on Sep. 5, 2000, now Pat. No. 6,474,143.

(51) Int. Cl.$^7$ .............................. G01N 9/32; G01N 11/06
(52) U.S. Cl. .................... 73/54.01; 73/32 R; 73/54.02; 73/54.07; 73/433; 73/451
(58) Field of Search ............................ 73/32 R, 54.01, 73/54.02, 54.07, 54.11, 433, 434, 435, 436, 451

(56) References Cited

U.S. PATENT DOCUMENTS

| 2,132,015 | A | 10/1938 | Collins ...................... 73/54.13 |
| 2,238,758 | A | 4/1941 | Thornhill ................... 73/54.07 |
| 2,252,014 | A | 8/1941 | Lupfer ....................... 73/54.02 |
| 3,074,266 | A | 1/1963 | Sadler ........................ 73/54.13 |
| 5,052,219 | A | 10/1991 | Fery et al. |

Primary Examiner—Daniel S. Larkin
(74) Attorney, Agent, or Firm—G. Turner Moller

(57) ABSTRACT

A drilling mud monitoring system includes a single measurement chamber which is filled with a predetermined quantity of drilling mud. The chamber is weighed to provide a value representative of the density of the drilling mud. The time needed for the chamber to drain is measured to provide a value representative of viscosity. The system proceeds through a measurement cycle in which the chamber is filled, weighed, timed and washed. At the end of the wash step, the weight of the chamber is compared with an empty weight and if the chamber weighs too much, the conclusion is that drilling mud adheres to the chamber so it is washed again. An alarm is sounded if the mud weight is too low and/or too high or in the case of a machine malfunction.

6 Claims, 3 Drawing Sheets

MONITORING LIQUID CHARACTERISTICS INCLUDING QUALITY CONTROL

This application is a divisional application of U.S. application Ser. No. 09/655,048, filed Sep. 5, 2000, now U.S. Pat. No. 6,474,143, entitled AUTOMATICALLY MONITORING DRILLING MUD.

This invention relates to a method and apparatus for automatically monitoring the density and viscosity of a liquid, such as drilling mud.

BACKGROUND OF THE INVENTION

Drilling fluids used to drill wells into the earth are commonly called drilling muds because the original drilling fluid was simply water that mixed with clays in the earth to produce a thin natural mud. Typically, drilling mud is pumped down the drill string, through nozzles in the end of the bit and then upwardly in the annulus between the drill string and the wall of the bore hole. Drilling mud has a variety of functions and must accordingly have comparable capabilities. Cuttings generated by the bit are moved away from the bottom of the hole and then upwardly through the annulus to the surface to present a clean rock face to be drilled. The bit is cooled and lubricated by the drilling mud. The mud also forms a wall cake on the exposed face of the well bore to prevent the drilled formations caving into the bore hole. The pressure of fluids in the formations penetrated by the bit is counterbalanced, or at least partially so, by the hydrostatic weight of the mud column in the hole. The drilling mud is modified to prevent undue effects on the bore hole wall, e.g. to prevent shale swelling. In water based muds, materials are added to prevent undue water loss into permeable formations penetrated by the bit. Various materials are added to reduce friction between the drill string and the bore hole wall. An almost endless list of substances have been added to drilling mud for a variety of reasons.

Two important characteristics of drilling mud are mud weight and viscosity. Mud weight is important to counterbalance the pressure in permeable formations penetrated so the well does not blow out. In English measurement systems, mud weight is reported in pounds per gallon. Most wells are drilled overbalanced, i.e. the mud weight is sufficient to contain formation pressures. Some wells are drilled underbalanced, i.e. the mud weight is not sufficient to wholly contain formation pressures, so the contents of drilled formations flow into the bore hole and are circulated to the surface. When it is desired to drill overbalanced, mud weights that are too low cause a well to kick or blow out. When it is desired to drill overbalanced, mud weights that are too high normally produce only unnecessary costs although there is a slight danger of causing formations up the hole to break down and take mud. When it is desired to drill underbalanced, mud weights that are too low create an excessive pressure differential across the formation face. When it is desired to drill underbalanced, mud weights that are too high may result in drilling the well overbalanced. In any event, abrupt changes in mud weight are a reliable signal that something is amiss and, in some situations, is a sign that disaster is approaching.

Mud weight is conventionally measured with a beam balance having a small metal cup at one end receiving a fixed amount of mud and a sliding weight on a lever arm fixed to the cup. The beam is placed on a pivot and the sliding weight moved along the lever arm until it balances. The density of the mud is read off the lever arm adjacent the slide. Mud weight is controlled by the addition of weight materials to the mud, usually barite which is a naturally occurring barium sulfate or hematite which is an iron oxide.

Viscosity of drilling mud is important because it is a measure of the capacity of the mud to move cuttings up the hole and a measure of the gel strength of the drilling mud which is related to the thixotropic capacity of the mud, i.e. the ability to set up as a gel or semi-solid thereby suspending cuttings to prevent them from settling to the bottom of the bore hole when the mud is quiescent. Viscosity is conventionally measured by adding a predetermined quantity of mud to a funnel of predetermined shape, known as a viscosimeter, Saybolt funnel, or viscosity funnel, allowing the predetermined volume to run out of the funnel, and measuring the time for the funnel to empty. Viscosity of drilling mud is typically measured in seconds. With low cost, water based muds, viscosity is controlled by the addition of bentonite which is often called gel. Bentonite is a naturally occurring swellable clay and has been used for decades as the standard viscosifier in drilling muds. Many other materials, such as polymers, are also commonly used.

Drilling mud has many other properties that are measured by a technician known as a mud man. These properties include water loss, pH, gel strength, and the like. Although these properties are of importance for a variety of different reasons, to the drilling contractor or person responsible for drilling the well and delivering a logable hole at the least cost, the most important mud characteristics are mud weight and viscosity.

It is known in the art to automatically monitor mud weight and/or viscosity of drilling mud as shown in U.S. Pat. Nos. 2,132,015; 2,252,014; 3,074,266; and 5,052,219.

SUMMARY OF THE INVENTION

In this invention, an automated device is provided to periodically measure the density and viscosity of any suitable liquid, such as solutions, slurries, or suspensions of any type, for example drilling mud, paint, and the like. Although the method and apparatus of this invention are applicable to other liquids, this invention is described in conjunction with drilling mud because that is a particular niche for which the invention has application.

A suitable print out is provided, preferably at a remote location, such as the driller's station, a central office, or a location handy to a drilling consultant. An important feature of this invention is using a single container to weigh a quantity of mud and measure the time it takes for the mud to drain out of the container thereby providing a measure of viscosity.

A variety of features allow the device of this invention to produce consistently reliable results: (1) the measuring container is washed at the end of every measurement cycle and, if the weight of the container does not fall to a predetermined empty weight, the container is rewashed; (2) if rewashing does not reduce the weight of the container to its empty weight, the conclusion is that mud solids have adhered to the container which can corrupt subsequent measurements and an alarm is accordingly sounded and the device turned off; (3) an alarm is sounded if the mud weight measures a value which is too low and/or too high; (4) the too low weight and/or the too high weight limits can be set by an operator; (5) in the event the measuring container overflows, the device is shut off and an alarm sounded; (6) when the supply valve to the mud container opens, the weight of the container is monitored so that, if the weight of the container does not increase, the conclusion is made that something is amiss with the supply valve and/or there is a blockage in the mud line; (7) multiple weight measurements are taken and then averaged to provide the reported mud weight; and (8) a relatively large volume of mud is weighed, as compared to the conventional beam balance thereby providing greater accuracy because small errors are not magnified by the multiplication that necessarily goes on to convert the measured value to pounds per gallon.

It is an object of this invention to provide an improved method and apparatus for automatically monitoring drilling mud.

Another object of this invention is to provide a method and apparatus for measuring the density and viscosity of drilling mud.

A further object of this invention to provide apparatus for monitoring drilling mud which is inexpensive and reliable and which produces consistent results.

Another object of this invention is to provide an apparatus for measuring drilling mud weight and viscosity which employs a single measuring container.

These and other objects and advantages of this invention will become more fully apparent as this description proceeds, reference being made to the accompanying drawings and appended claims.

DETAILED DESCRIPTION

Figure 1:
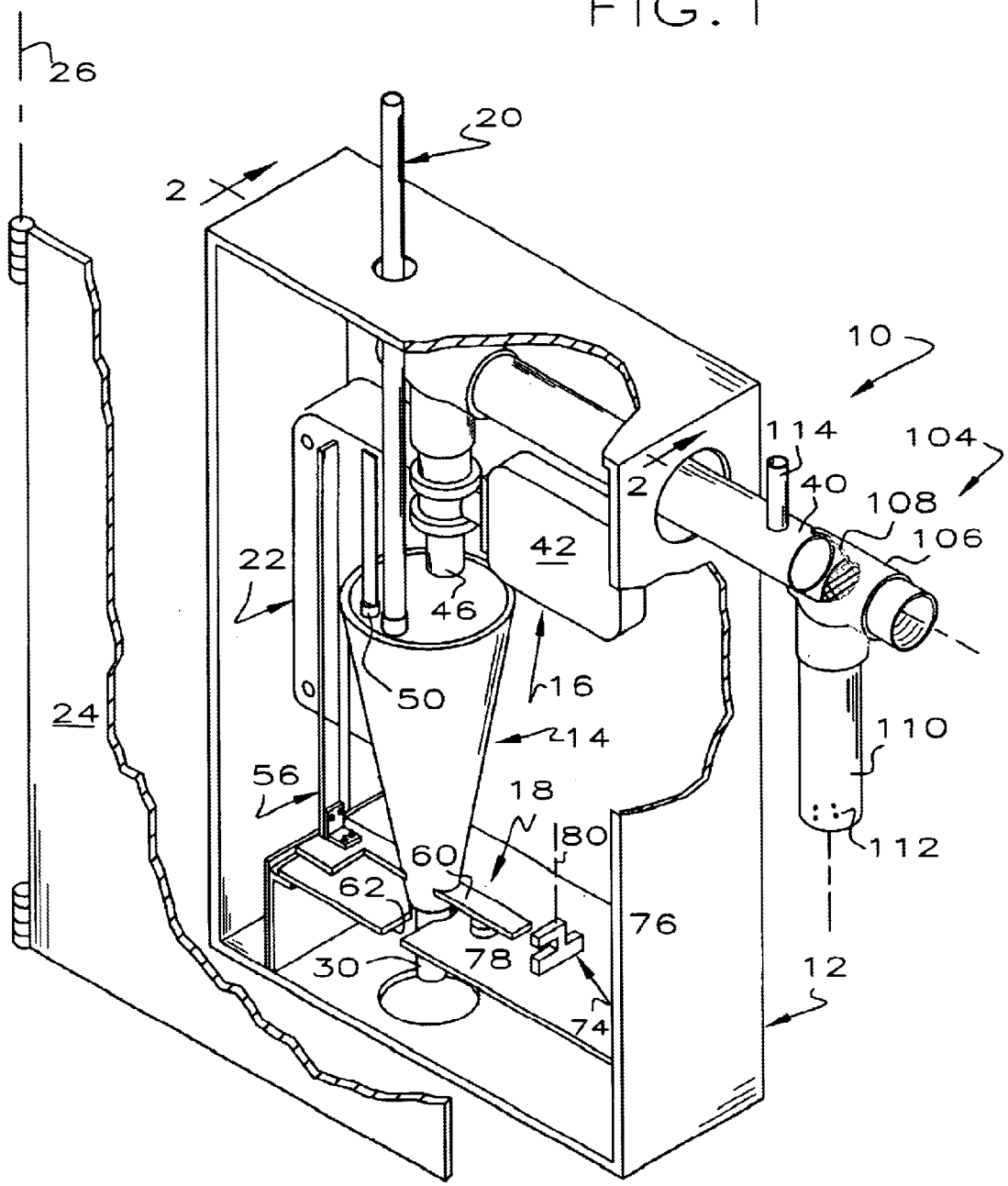
FIG. 1 is an isometric view of the apparatus of this invention.
Figure 2:
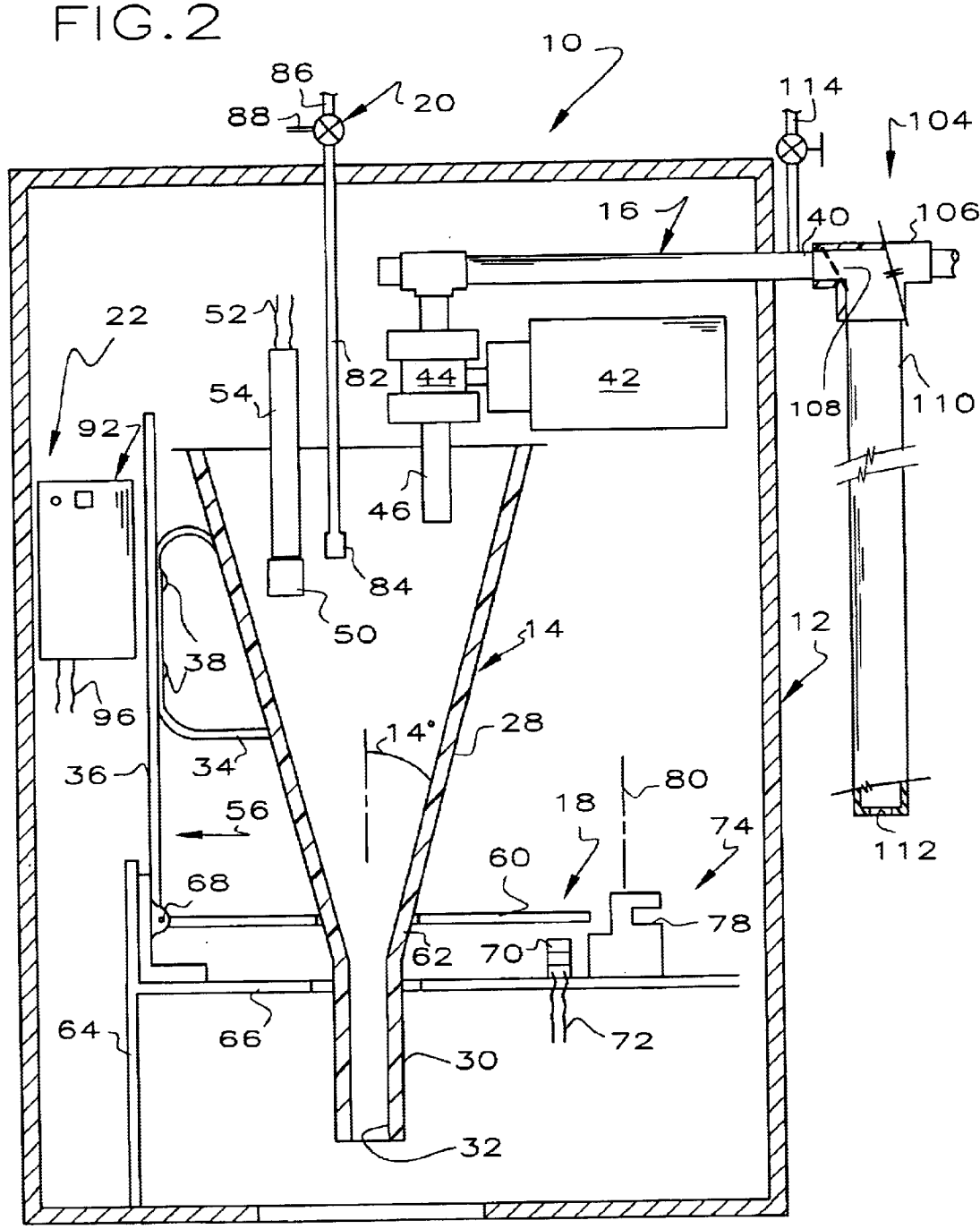
FIG. 2 is an enlarged cross-sectional view of the device of FIG. 1, taken substantially along line 2—2 as viewed in the direction indicated by the arrows.
Figure 3:
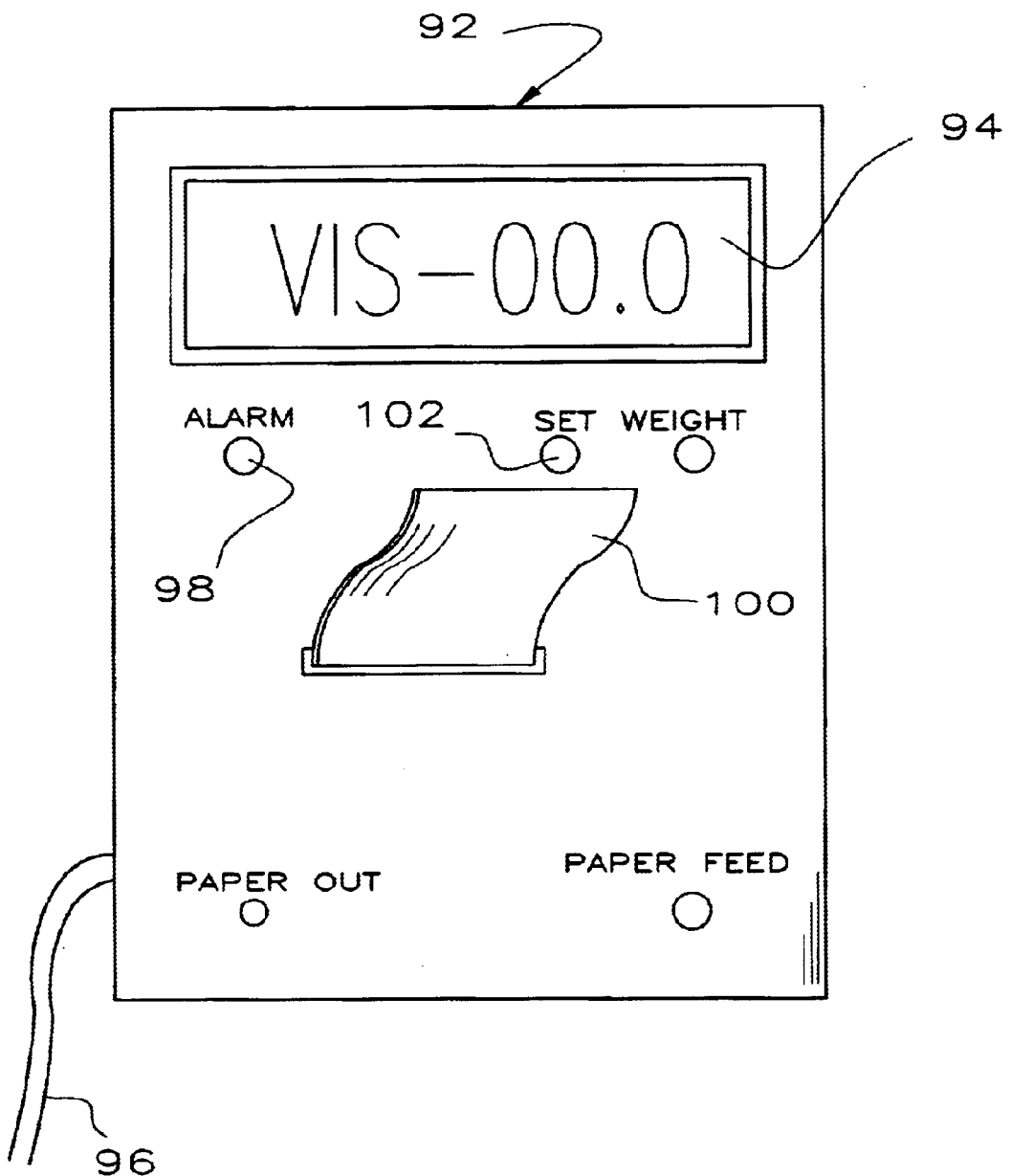
FIG. 3 is a front view of a recorder used with this invention.

Referring to FIGS. 1–2, a mud monitoring device 10 of this invention comprises, as major components, a housing 12, a chamber or funnel 14 for receiving a quantity of drilling mud, means 16 for delivering a predetermined quantity of mud to the chamber 14, means 18 for weighing the chamber 14, means 20 for washing the chamber 14, and means 22 for controlling operation of the device 10 including monitoring the weighing means 18 and measuring the time for the chamber 14 to drain.

The housing 12 is of conventional design and includes a metallic or plastic box having a door 24 mounted for pivotal movement on an axis 26. A suitable latch or lock (not shown) releasably attaches the door in a closed position.

The chamber 14 is preferably in the shape and size of a standard Saybolt or viscosity funnel conventionally used to measure drilling mud viscosity. A standard Saybolt or viscosity funnel has a generally frustoconical shaped side or bottom wall 28, has an outlet 30 providing an opening 32 that is 0.180 inches in inside diameter, is 14.25 inches tall, and has a slope of 14°. In a conventional viscosity measuring technique, one quart of liquid is poured into the funnel 14 with a finger closing the outlet opening 32. The user would remove the finger from the outlet opening 32 and measure the time, usually with a wrist watch, needed for the funnel 14 to empty.

Ideally, the chamber 14 is a standard Saybolt or viscosity funnel in which the handle 34 is attached to an element 36 of the weighing means 18 by fasteners 38 as will be described more fully apparent hereinafter. Using the standard Saybolt or viscosity funnel as the weighing chamber 14 is an ideal approach because the viscosity of the drilling mud can be determined simply by measuring the time for the funnel to drain which is necessarily part of the weighing cycle.

The mud delivery means 16 includes a conduit 40 connected to a mud line of the drilling rig (not shown) with which this invention is used. Desirably, the monitoring device 10 is placed in the mud line leading from the well and a second monitoring device is placed in the mud line leading to the well. In this manner, mud weight and viscosity are measured after the mud is treated and before it is pumped into the well and after the mud exits from the well. The device 10 that measures mud coming from the well is preferably placed upstream of any shale shaker or the like where treatment of the mud affects mud weight and/or viscosity. When placed upstream from the shale shaker, it is desirable to provide a screen through which the liquid mud flows to the device 10 while allowing large solids to bypass the device 10, as will be pointed out more fully hereinafter.

When the control means 22 starts a measurement cycle, a signal is sent to a valve motor 42 which opens a valve 44 thereby delivering drilling mud through an outlet 46 into the funnel 14. Because mud flow into the funnel 14 is much greater than mud flow out of the opening 32, the funnel 14 fills. The rate of filling is the difference between the inflow rate through the valve 44 and the outflow rate through the opening 32. When the liquid in the funnel 14 reaches a predetermined level, the controller 22 sends a signal to the valve motor 42 to close the valve 44. The liquid level in the funnel 14 is sensed by a sensor 50 of any suitable type providing a signal to the controller 22 over outlet wires 52 which conveniently pass through a metallic support 54 supporting the sensor 50. The sensor 50 may be a float operated switch, an ultrasonic liquid level detector, or the like. The support 54 may be adjustable to provide a means of adjusting the position of the sensor 50.

The weighing means 18 includes an L-shaped support 56 to which the chamber 14 is fixed. The support 56 includes the vertical element 36 to which the funnel handle 34 is fixed and a horizontal element 60 having an passage 62 opening through the forward edge of the element 60. The lower end of the funnel 14 extends through the passage 62 and can be removed by deforming the plastic body of the lower end of the funnel 14 and pulling it through the passage 62. The support 56 is mounted on an arm 64 extending upwardly from a horizontal wall 66 for pivotal movement about an axis 68. The free end of the horizontal element 60 is accordingly mounted for movement between an operative position abutting a load cell 70 which senses the load applied by the support 56, the empty funnel 14, and any drilling mud in the funnel. The load cell 70 connects to the controller 22 by suitable wires 72.

A lock out mechanism 74 is provided to support the element 60 out of contact with the load cell 70 to allow the device 10 to be transported without damaging the load cell 70. The mechanism 74 accordingly includes a rigid body 76 having a slot 78 of a size to receive the end of the horizontal element 60. The body 76 is mounted for rotational movement about a vertical axis 80 so the slot 78 moves to a position out of engagement with the element 60 allowing the device 10 to operate and into a position supporting the element 60 thereby preventing damage to the load cell 70 during handling.

The washing means 20 includes a conduit 82 connected to a source of relatively clean wash liquid, such as water or diesel fuel, as is available on any drilling rig. Water is used as the wash liquid when the mud is a water based mud, and diesel fuel is used when the mud is an oil emulsion. A spray nozzle 84 is positioned below the top of the funnel 14 and above the level of liquid sensed by the sensor 50 to start weighing and viscosity measurements. The nozzle 84 delivers a large quantity of clean wash liquid to rinse and thereby clean the inside of the funnel 14. The washing means 20 is controlled by a suitable valve 86 operated by a solenoid or other conventional operator receiving a signal along wires 88 from the controller 22.

A description of the operation of the device 10 reveals a number of important features. It is preferred that the drilling mud be monitored at relatively frequent intervals, e.g. every fifteen minutes. The time between measurement cycles can be incorporated into the controller or may be set in the field in any suitable fashion, as by an input (not shown) on the controller 22 or on a recorder 92.

At the beginning of a measurement cycle, a signal passes from the controller 22 to the valve motor 42. Because the funnel outlet opening 32 is restricted, the funnel 14 fills rather rapidly and is not particularly flat. For this reason, the sensor 50 detects a rising liquid level in the funnel 14 and the controller 22 closes the valve 44 in response to the rising liquid level. Because of the time delay and because of the volume of liquid in the outlet 46 downstream of the valve, the liquid level in the funnel 14 rises slightly after the sensor 50 detects the liquid level which is selected to shut off the valve 44. After flow into the funnel 14 stops, the liquid surface in the funnel 14 flattens out and relatively slow flow through the funnel outlet 30 causes the liquid surface to become reasonably flat. As the liquid level in the funnel falls, the sensor 50 detects a predetermined value which is recognized by the controller 22 and used to initiate weighing.

Modern load cells are capable of making a large number of measurements in a very short time, e.g. one hundred measurements in a nanosecond. In a nanosecond, very little liquid flows through the restricted outlet opening 32 so a large number of measurements can be made and averaged. Preferably, values which are abnormally high or low can be discarded before averaging the balance. Ideally, the high 5% of the measured values and the low 5% of the measured values are discarded and the balanced averaged to provide a measurement which is transmitted by the controller to a suitable display 94 on the recorder 92 through wires 96 or through a wireless transmitter (not shown). The recorder 92 may be of any suitable type and one may be located at the driller's station, in a central office location or in a trailer, or other location suitable for a drilling consultant.

An important feature of this invention is measuring the chamber 14 when it is empty which is included to mean when it is dry or when it is water wet. This measurement is necessary to determine the density of the mud being monitored because one gets a value from the load cell 70 representative of a full weight and a deduction needs to be made for an empty weight.

The liquid level sensed by the sensor 50 to measure the weight of the mud in the funnel 14 is conveniently, but not necessarily, used to measure viscosity. In other words, the liquid level sensed by the sensor 50 as mud is running out of the funnel is the liquid level corresponding to the predetermined volumetric capacity, e.g. one quart, in the funnel. It should be understood, of course, that different liquid levels could be used for weight and viscosity measurements with the necessary adjusting calculations being made by the controller 22. Viscosity is accordingly simply measured by measuring the time needed for the weight of the funnel to fall from the full weight to the empty weight. In the event the measured weight of the funnel does not fall to the empty weight within a reasonable time, e.g. two minutes, the conclusion is there is some reason the funnel has not emptied, such as a shale particle stuck in the outlet opening. The washing means 20 is turned on to rinse the funnel and the measuring cycle is repeated before recording any of the values. In the event the empty weight on the next measuring cycle does not fall to the empty weight within a reasonable time, an alarm 98 at the recorder 92 is sounded, a message is printed out at the recorder 92, and the device 10 turned off.

By weighing the funnel 14 when it contains a predetermined large volume, e.g. one or more quarts, the density of the mud in pounds per gallon is obtained simply by multiplying the difference between the full weight and empty weight of the funnel by a factor which is sufficient to raise the volume to a gallon. A preferred volume for the funnel 14 is one quart, which is the volume necessary for a conventional viscosity measurement. The factor necessary to raise the volume to a gallon is accordingly four. Thus, any error in the weighing operation is magnified, using the preferred volume of one quart, only by a factor of four. In a conventional mud weighing balance, the cup capacity is only about four fluid ounces so the multiplication factor is thirty two. Thus, any measurement error in a conventional mud balance is magnified to a much greater extent than in this invention.

If viscosity is successfully measured, the date, time of day, mud weight, and viscosity are printed out on a paper 100 exiting from the recorder 92.

At the end of a successful measurement cycle, the controller 22 turns on the washing means 20 to rinse away any drilling mud on the inside of the funnel 14. The load cell 70 continually measures the load on the horizontal element 60 in the sense that the element 60 continually bears on the load cell 70. Thus, the weight of the funnel is measured at the end of the wash cycle. In the event the weight of the funnel 14 returns to the empty weight, the conclusion is that the funnel is clean and the device 10 is ready for another measurement cycle. In the event the weight of the funnel does not fall to the empty weight, the conclusion is that the funnel contains some drilling mud residue and the washing means 20 is turned on again. If the weight of the funnel returns to the empty weight, the conclusion is that the funnel is clean and the device 10 is ready for another measurement cycle. In the event the weight of the funnel again does not fall to the empty weight, a message to this effect is printed on the paper 100 by the recorder 92, the alarm 98 is sounded and the device 10 is turned off.

The device 10 is capable of setting off the alarm 98 in the event mud weight falls too low or becomes too high. Ideally, this value may be set at the recorder 92 by an input 102.

The device includes other features promoting consistently reliable results. In the event the funnel 14 overflows, this condition is detected because the weight of the funnel increases to a point and then stops at a time when the valve 44 is open and the sensor 50 has not yet indicated that the predetermined level is reached. The conclusion is that the sensor 50 has malfunctioned so the alarm 98 is sounded, a message is printed on the paper 100, and the device 10 is turned off.

When the supply valve 44 is open and the weight of the container does not increase, the conclusion is that something is amiss with the supply valve and/or there is a blockage in the conduit 40, or in a screen assembly 104 through which mud flows into the conduit 40, or that mud flow has stopped for a substantial time for some other reason. After a delay of a few minutes, a message is printed on the paper 100 and the alarm 98 sounded. To avoid sounding the alarm during an intended interruption of mud flow, as when making a connection, several options are feasible. The conduit 40 may connect to a part of the mud system where an accumulation of mud exists, e.g. to the inlet box of a shale shaker. In the alternative, a connection may be made from the controller 22 to the rig pumps so that when the rig pumps are stopped, no measurements are taken.

Referring to FIGS. 1–2, a screen assembly 104 is provided to remove drilled solids, such as large shale particles, from the mud upstream of the device 10. The screen assembly 104 comprises a tee 106 in the conduit 40, an inclined screen 108 in the tee, and a drain 110 leading off from the tee 106 providing a restricted drain hole 112. When the supply valve 44 is closed, mud passes through the tee 106, through the drain 110, and out through the drain hole 112. When the supply valve 44 opens, mud flows through the screen 108. Any large particles are rejected by the screen 108 and drop into the drain 110. It would appear that mud located between the tee 106 and the valve 44 is old mud and its presence would affect readings taken by the device 10. In practice, the volume of mud in the line 40 between the valve 44 and the tee 106 is very small and it flows out of the bottom of the funnel 14 well before any measurements take place. At the end of a measurement cycle, a supply of wash liquid is delivered through a conduit 114 as controlled by a suitable valve 115 to wash any drilled solids collecting on the screen back into the drain 110.

When the valve 44 is closed, all flow toward the device 10 is diverted to the drain 110. When the valve 44 opens, almost all flow is diverted to the device 10 because the restricted drain opening 112 provides a much greater restriction to flow than does the valve 44 and piping downstream of the screen assembly 104.

Although this invention has been disclosed and described in its preferred forms with a certain degree of particularity, it is understood that the present disclosure of the preferred forms is only by way of example and that numerous changes in the details of operation and in the combination and arrangement of parts may be resorted to without departing from the spirit and scope of the invention as hereinafter claimed.

I claim:

1. An apparatus for monitoring density and viscosity of a liquid, comprising:

a measuring container for receiving the liquid;

an inlet for connection to a source of the liquid and having a valve for filling the container;

an assembly for obtaining the weight of the container and thereby obtaining a value representative of the density of the liquid including an assembly for obtaining a weight of the container a multiplicity of times over a period of time to produce a first average weight at a first time and a second average weight at a second later time;

an assembly obtaining a value representative of the viscosity of the liquid; and an assembly for conducting quality control procedures using the first and second average weights of the container when the second average weight is less than the first average weight.

2. The apparatus of claim 1 wherein the assembly for obtaining a weight of the container a multiplicity of times is an assembly for obtaining the weight of the container a multiplicity of times during filling of the container and the quality control assembly is an assembly for conducting quality control procedures during filling.

3. The apparatus of claim 2 wherein the quality control assembly is an assembly measuring the weight of the container at a time when the valve is open.

4. The apparatus of claim 2 wherein the quality control assembly is an assembly measuring the weight of the container at a time when the valve is closed.

5. The apparatus of claim 1 further comprising an assembly for rinsing the container after weighing the container and an assembly for comparing the weight of the container after rinsing with an empty weight of the container and activating the rinsing assembly again if the weight of the container is more than the empty weight.

6. The apparatus of claim 5 further comprising an assembly for comparing the weight of the container after a subsequent rinsing of the container and sounding an alarm if the weight of the container is more than the empty weight.

* * * * *